July 5, 1966 R. KORDES Plant Pat. 2,651
ROSE PLANT
Filed Aug. 17, 1965
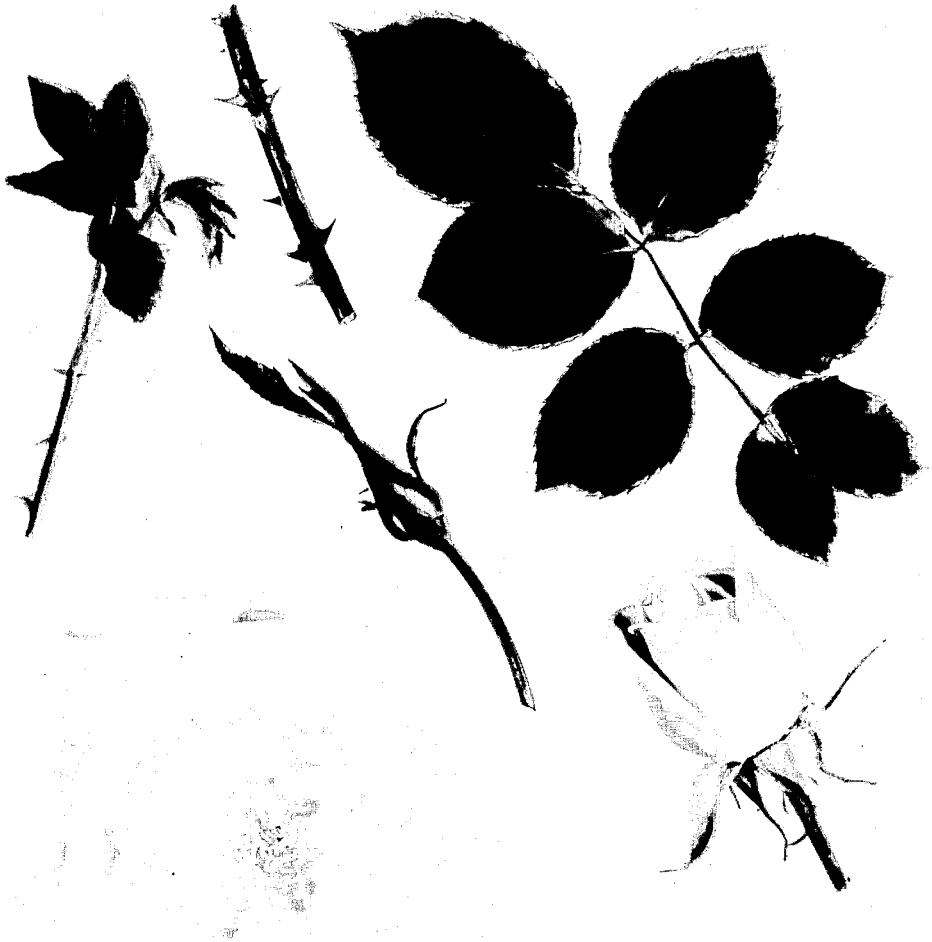
Inventor.
Reimer Kordes
By. Robb & Robb
Attorneys.

United States Patent Office

Plant Pat. 2,651
Patented July 5, 1966

2,651
ROSE PLANT

Reimer Kordes, Barmstedt, near Elmshorn, Germany, assignor to Jackson & Perkins Company, Newark, N.Y., a corporation of New York

Filed Aug. 17, 1965, Ser. No. 480,534
1 Claim. (Cl. Plt.—16)

The present invention relates to a new and distinct variety of rose plant of the hybrid tea class, which was originated by me by crossing the hybrid tea variety known as "Goldene Sonne" (unpatented) with the hybrid tea variety known as "Chantre" (unpatented).

The primary objective of this breed was to produce a new rose variety which bears large bronze colored flowers of hybrid tea form and which retains the color without fading. This objective was fully achieved, as evidenced by the following unique combination of characteristics which are outstanding in the new variety and distinguish it from its parents, as well as from all other varieties of which I am aware:

(1) A healthy habit of growth;
(2) A very large flower size;
(3) Good flower petalage; and
(4) A distinctive and attractive flower color beginning as Scarlet in the bud stage, but changing in the open flower to Orange-Buff, with the outer edges of the petals overcast with Light Orange-Yellow, said colors being retained to the end of the flower.

Asexual reproduction of the new variety by budding, as performed at Newark, New York, U.S.A., and also at Pleasanton, California, U.S.A., shows that the foregoing characteristics and distinctions come true to form and are established and transmitted through succeeding propagations.

The accompanying drawing shows typicals specimens of the vegetative growth and flowers of my new variety in different stages of development and as depicted in color as nearly true as it is reasonably possible to make the same in a color illustration of this character.

The following is a detailed description of the new variety with color terminology in accordance with Ridgway's Color Standards and Nomenclature:

Parentage: Seedling.
*Seed parent.*—"Goldene Sonne."
*Pollen parent.*—"Chantre."
Classification:
*Botanic.*—Hybrid tea.
*Commercial.*—Hybrid tea.

*Flower*

(Observations made from specimens grown outdoors at Newark, New York, U.S.A., near mid-morning during the month of September.)

Blooming habit: Recurrent—continuous.
Bud:
*Size.*—Large.
*Form.*—Ovoid-pointed; is not affected by wet or hot weather.
*Color.*—When sepals first divide—Empire Yellow, Plate 4. When petals begin to unfurl—Scarlet-Red, Plate 1. When half-blown: Inside of petals—Scarlet, Plate 1; reverse of petals—Grenadine Red, Plate 2, overcast with Flame Scarlet, Plate 2.
*Sepals.*—Smooth edge; curl back when petals begin to unfurl. Color: Inside—Kildare Green, Plate 31; outside—Cress Green, Plate 31.
*Calyx.*—Color—Cress Green, Plate 31. Shape—apple. Size—large. Aspect—smooth. Odor when rubbed—none.

*Peduncle.*—Length—long. Aspect—rough. Strength—erect; heavy. Color—Cerro Green, Plate 5, very lightly overcast with Pompeian Red, Plate 13.
*Opening.*—Opens up well; is not affected by adverse weather conditions.
Bloom:
*Size.*—Very large. Average size when fully expanded—6 inches.
*Borne.*—Both singly and several together.
*Stems.*—Long; strong.
*Form (when first open).*—High-centered. Permanence—retains its form to the end, but outer petals curl back.
*Petalage.*—Double (full but open center). Number of petals under normal conditions—from 40 to 45.
*Color.*—Center of flower—Flame Scarlet, Plate 2. Outer petals—Pale Orange-Yellow, Plate 3, with outer edge of petals lightly overcast with Orange-Buff, Plate 3. Base of petals (aiglet)—Lemon Chrome, Plate 4. Inside of petals—Orange-Buff, Plate 3, with outer edge of petals overcast with Light Orange-Yellow, Plate 3. Reverse of petals—Orange-Pink, Plate 2, overcast with Strawberry Pink, Plate 1. General tonality from a distance—Orange-Buff, Plate 3, with outer edge of petals overcast with Light Orange-Yellow, Plate 3.
*Discoloration.*—General tonality at end of first day—Orange-Buff, Plate 3, with outer edge of petals overcast with Light Orange-Yellow, Plate 3. Second day—Orange-Buff, Plate 3, with outer edge of petals overcast with Light Orange-Yellow, Plate 3. Third day—Pale Orange-Yellow, Plate 3, with outer edge lightly overcast with Orange-Buff, Plate 3.
Petals:
*Texture.*—Thick; is not affected by wet or hot weather.
*Appearance.*—Inside—shiny. Outside—satiny.
*Form.*—Oval; slightly notched.
*Arrangement.*—Imbricated (regularly arranged shingle-like).
*Petaloids in center.*—Few; large.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Large size; many; regularly arranged around styles. Color—Light Orange-Yellow, Plate 3.
Stamens, Filaments (threads): Long. Color—Light Cadmium, Plate 4.
Pollen: Color—Pale Yellow-Orange, Plate 3.
Styles: Loosely separated; uneven length; medium length; thin.
Stigmas: Color—Buff-Yellow, Plate 4.
Ovaries: All enclosed in calyx.
Hips: None.
Seeds: None.

*Plant*

Form: Bush.
Growth: Vigorous; upright.
Foliage: Compound of 5–7 leaflets.
*Size.*—Large.
*Quantity.*—Abundant.
*Color.*—New foliage: Upper side—Yellowish-Oil Green, Plate 5, with serrations Oxblood Red, Plate 1; under side—Parrot Green, Plate 6, lightly overcast with Oxblood Red, Plate 1, on the outer edge of the petals. Old foliage: Upper side—Empire Green, Plate 32; under side—Light Cress Green, Plate 31.

*Shape.*—Oval pointed.

*Texture.*—Upper side—leathery and glossy. Under side—smooth.

*Ribs and veins.*—Ordinary.

*Edge.*—Serrated (saw toothed).

*Serration.*—Both double and single; sharp.

*Leaf stem.*—Color—Cerro Green, Plate 5, very lightly overcast with Acajou Red, Plate 13. Under side—prickly.

*Stipules.*—Medium length; smooth.

Wood:

*New wood.*—Color—Deep Chrysolite Green, Plate 31. Bark—smooth.

*Old wood.*—Color—Cress Green, Plate 31. Bark—smooth.

Thorns:

*Thorns.*—Quantity: On main stalks from base—ordinary; on laterals from stalk—ordinary. Form—narrow base; medium length; hooked downward. Color (when young)—Eugenia Red, Plate 13. Position—Irregular.

*Prickles.*—Quantity: On main stalks—none; on laterals—none.

*Short needles.*—Quantity: On main stalks—none; on laterals—none.

I claim:

A new and distinct variety of rose plant of the hybrid tea class, substantially as herein shown and described, characterized particularly as to novelty by the unique combination of a healthy habit of growth, a very large flower size, good flower petalage, and a distinctive and attractive flower color beginning as Scarlet in the bud stage, but changing in the open flower to Orange-Buff, with the outer edges of the petals overcast with Light Orange-Yellow, said colors being retained to the end of the flower.

No references cited.

ABRAHAM G. STONE, *Primary Examiner.*

R. E. BAGWILL, *Assistant Examiner.*